United States Patent [19]

Gross et al.

[11] 4,432,759
[45] Feb. 21, 1984

[54] CONNECTING DEVICE FOR MEDICAL LIQUID CONTAINERS

[75] Inventors: James R. Gross, Bartlett; Albert F. Bujan, Waukegan, both of Ill.

[73] Assignee: Abbott Laboratories, North Chicago, Ill.

[21] Appl. No.: 371,643

[22] Filed: Apr. 26, 1982

[51] Int. Cl.³ ............................................. A61M 5/00
[52] U.S. Cl. ................................... 604/411; 604/905; 285/419
[58] Field of Search ............................ 604/27–29, 604/280, 283, 403, 408–411, 412, 415, 905, 413, 414; 251/149.1, 149.9; 285/DIG. 2, 3, 260, 38, 27, 45, 373, 423, 21, 419; 215/249, 251, 274, 247

[56] References Cited

U.S. PATENT DOCUMENTS

| | | | |
|---|---|---|---|
| 3,394,954 | 7/1968 | Sarns | 285/319 |
| 4,161,949 | 7/1979 | Thanawalla | 604/905 X |
| 4,306,976 | 12/1981 | Bazzato | 604/29 X |
| 4,340,052 | 7/1982 | Dennehey et al. | 128/247 X |
| 4,353,367 | 10/1982 | Hunter et al. | 604/905 X |
| 4,354,490 | 10/1982 | Rogers | 604/905 X |
| 4,366,816 | 1/1983 | Bayard et al. | 604/905 X |

Primary Examiner—C. Fred Rosenbaum
Assistant Examiner—Michelle N. Lester
Attorney, Agent, or Firm—Robert S. Beiser; Alan R. Thiele

[57] ABSTRACT

A connecting device for medical liquid administration sets, particularly for use in continuous ambulatory peritoneal dialysis comprises a tubular port extending from a medical liquid container. The tubular port has a pierceable diaphragm positioned within and sealing the same. A hollow tubular piercing pin having a sharpened tip is used for penetrating the pierceable diaphragm. A length of flexible tubing extends from the piercing pin and is connected to a catheter positioned in the peritoneum of the patient. A locking mechanism is utilized for selectively retaining the piercing pin within the tubular port following insertion, and for asepticizing the connection. The locking mechanism comprises a tubular clasp which closes around the piercing pin and telescopes over the tubular port. A plurality of ratchets on the inside of the clasp lock the pin and port together following connection.

5 Claims, 2 Drawing Figures

CONNECTING DEVICE FOR MEDICAL LIQUID CONTAINERS

BACKGROUND OF THE INVENTION

The present invention relates generally to the field of connecting mechanisms for fixedly joining together a length of tubing to a medical liquid container. Connectors of this general type are capable of a wide variety of uses in medical applications. The connector of the present mechanism was developed specifically for use in continuous ambulatory peritoneal dialysis.

Connectors have been used for many years to effectuate rapid and effective junctions between pieces of tubing. A requirement of such connectors is that a fluid-tight seal be obtained. Another requirement is that the connection, once made, should be strongly resistant to inadvertent disengagement, but should be readily disengageable when desired by simple and rapid manual manipulation.

It has long been known that fluid-tight connections are provided by a pair of tapered members, one including a female portion having an internal opening with an inner conical tapered sealing surface, and the other member including a male portion having a protrusion with an outer conical, matingly tapered, sealing surface. However, in order to ensure the desired fluid-tight connection, the members must be forced longitudinally together, preferably with a slight twisting motion, with sufficient pressure to ensure that the locking friction angle of the tapered surfaces are forced into intimate frictional contact. Even when the desired intimate contact providing the fluid-tight connection is established, an inadvertent, longitudinal tugging between the tubes associated with the two members is often sufficient to disengage the connection and break the seal.

Similarly, the use of piercing pins adapted for connection to medical liquid containers is commonly known in the art. However, such piercing pins are commonly inserted into a length of flexible tubing extending from the containers in a press-fit connection which is difficult to disengage while in use. Thus, the problem heretofore unsolved by the prior art is the provision of simplified means to ensure the intimate frictional contact sufficient to provide fluid-tight connection and to preclude relative longitudinal motion tending accidentally to disengage the sealing surfaces, while at the same time allowing selective disengagement with relatively easy manual manipulation. At the same time, maintaining the connection in an aseptic condition is also desirable.

Examples of attempts to overcome this problem are the devices shown in U.S. Pat. Nos. 4,201,406; 4,030,494; and U.S. No. De. D-229,518. Despite these efforts, in the field of peritoneal dialysis, a relatively high rate of peritonitis has been found, which, it is suspected, is due to the passage of microorganisms through the connector and into the peritoneal cavity of the patient. In order to prevent such microbial contamination, it is an advantage of the present invention to provide a novel connecting device which maintains the connection between a piercing pin and a container port in a sealed configuration. As an additional feature, the present connector may include an aseptic barrier positioned within the device which provides a barrier against the invasion of microbial contaminants. It is an additional advantage of the present invention to provide such a connecting device which is relatively easy to manipulate and inexpensive to manufacture.

SUMMARY OF THE INVENTION

The foregoing advantages are accomplished and the shortcomings of the prior art are overcome by the connecting device of the present invention, which comprises a tubular port member extending from a medical liquid container and having a pierceable diaphragm positioned within and sealing said port member. A hollow tubular piercing pin connected to a length of flexible tubing at its proximal end and having a sharpened tip at its distal end is adapted for penetrating the pierceable diaphragm. A locking mechanism is provided for selectively retaining the piercing pin within the tubular port member following such insertion.

The tubular port member may include a rigid tubular insert fixedly attached within and sealing the port. The rigid tubular insert has a circular flange extending concentrically therefrom which is designed to limit the insertion of the plug into the tubular port. Alternatively, the tubular port itself may include a concentric circular flange disposed about its distal end, adapted for connection to the locking mechanism previously mentioned. The tubular piercing pin also includes a similar circular flange for limiting the insertion of the piercing pin into the port.

The previously mentioned locking mechanism comprises a clasp member composed of first and second C-shaped portions, hingedly connected together. Each of the C-shaped members include oppositely disposed semicircular slots adapted for reception of and engagement with the piercing pin. The C-shaped portions of the clasp also include a latching mechanism so that when the clasp member is pivotally enclosed about the pin, the latch may be closed and locked. The clasp mechanism is designed to engage with the previously mentioned circular flanges so that the piercing pin and the port may not be moved longitudinally out of the clasp. As a result, the connecting device fixedly positions the piercing pin relative to the tubular port.

In a preferred embodiment the clasp includes a plurality of ratchets or teeth, pointing inward which allow the clasp to be telescopically joined with the tubular port, but once advanced beyond the flange on the port prevent separation without opening the clasp.

An additional feature of the clasp mechanism is the inclusion of antiseptic sponges or another absorbent medium in each of the C-shaped portions, constructed and arranged for asepticizing the connection between the tubular port and the piercing pin. This is accomplished by means of an antiseptic solution dispensed into the sponge, such as povidone iodine (Betadine). Other commonly known antiseptic solutions may also be used.

In a preferred embodiment, the clasp mechanism comprises a modular unit constructed of injection molded polypropylene or other thermoplastic propylene having an integrally formed flexible hinge between the first and second portions. The latch mechanism comprises an integrally formed latch on one of the C-shaped members and a slot constructed and arranged for reception of the latch on the opposing C-shaped member so that when the two C-shaped members are pivoted towards each other, the latch may be engaged into the opposing slot. The latch mechanism may also be selectively disengaged, as required.

DETAILED DESCRIPTION OF THE PREFERRED EMBODIMENT

Figure 1:
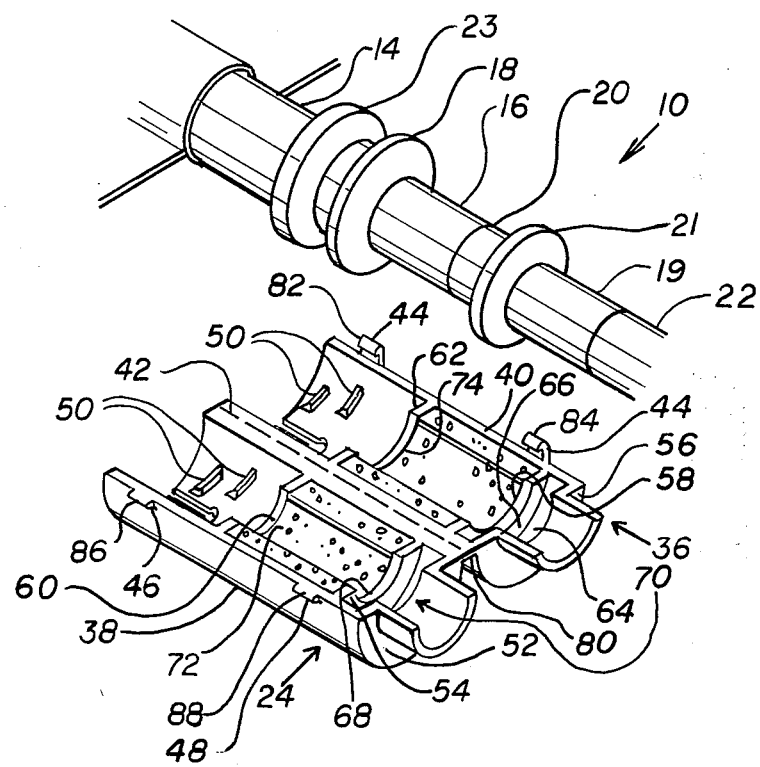
FIG. 1 of the drawings is a front perspective view of an improved connecting device for medical liquid containers.

While this invention is susceptible of embodiment in many different forms, there is shown in the drawings and will herein be described in detail, a specific embodiment, with the understanding that the present disclosure is to be considered as an exemplification of the principles of the invention and is not intended to limit the invention to the embodiment illustrated.

Figure 2:
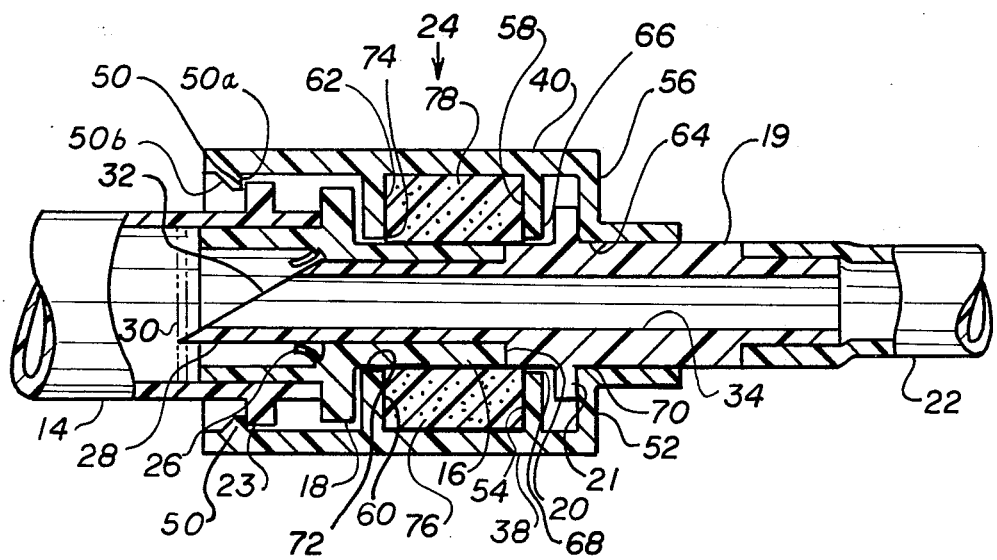
FIG. 2 of the drawings is a view in vertical section of the improved connecting device shown in FIG. 1 in a connected position.

As best seen in FIGS. 1 and 2 of the drawings, improved connecting device 10 for medical liquid container 12 is connected to a tubular port 14 extending from container 12. Extending from tubular port 14 is a rigid tubular insert 16 having a radial flange 18 concentrically disposed therearound. In order to provide access to liquid in container 12, a piercing pin 19 extends into tubular insert 16. Piercing pin 19 has a shoulder 20 concentrically disposed therearound and adapted for limiting the insertion of piercing pin 19 into insert 16. A length of flexible tubing 22 extends from piercing pin 19 and is adapted for the conveyance of liquid. Locking mechanism 24 is utilized to retain piercing pin 19 within tubular port 14.

As best seen in FIG. 2, disposed within tubular insert 16 is a pierceable diaphragm 26 which is penetrated by sharpened tip 28 of piercing pin 19 upon insertion into tubular port 14. Following such insertion, medical liquid contained within container 12 may pass from container 12, through tubular port 14, piercing pin 19, and out flexible tubing 22. Further seen in the drawings is radial circular flange 23 extending concentrically from tubular port 14 and adapted, with circular flange 18, for positioning locking means 24 relative thereto. Tubular port 14 may also include a pierceable diaphragm 30 disposed therein adapted for sealing of the port until penetration by piercing pin 19. In order to allow the flow of liquid through piercing pin 19, sharpened tip 28 has an open orifice 32 proximate thereto and opening into lumen 34 extending through piercing pin 19.

Returning to FIG. 1 of the drawings, locking mechanism 24, in a preferred embodiment, comprises a clasp member 36 which comprises first C-shaped portion 38 and second C-shaped portion 40, hingedly connected along midline 42 and including latching mechanisms 44 at opposing sides 46 and 48. Clasp member generally 36 is constructed and arranged for fixed positioning of piercing pin 19 relative to tubular port 14. A key aspect of the design of clasp 36 is inclusion of a series of ratchets 50 or protruding frictional engagement means within clasp 36 proximate the distal end thereof concentrically disposed therein. Ratchets 50 are arranged to slide over flanges 18 and 23 when piercing pin 19 and tubular port 14 are telescoped together. If piercing pin 19 and tubular port 14 are attempted to be subsequently pulled apart, ratchets 50 lock against flange 23, thereby preventing inadvertent disconnection. In order to assist in locking, semicircular end walls 52, 54, 56 and 58 extend into clasp 36 to enclose flange 21. Semicircular walls 60 and 62 also extend into clasp 36 proximate the middle thereof and are adapted for abutting against radial flange 18, so as to limit the telescoping joinder of clasp 36 onto tubular port 14. In order to allow enclosure of tubular port 14 and flexible tubing 22 by clasp member 36, semicircular slots 64, 66, 68, 70, 72 and 74 are oppositely disposed on first portion 38 and second portion 40 of clasp member 36. Thus, when clasp member 36 is pivotally enclosed about connecting device 10, semicircular slots 64, 66, 68 and 70 are radially disposed about piercing pin 19. A clamshell effect is thereby obtained. Pin 19 and tubular port 14 may be manually disconnected simply by opening clasp 36 and slidably disengaging port 14. Other commonly known latching mechanisms such as a tab insertable into a slot may also be used.

As an additional feature, as best seen in FIG. 1, antiseptic sponge members 76 and 78 are positioned within first C-shaped portion 38 and second C-shaped portion 40. In a preferred embodiment, sponge members 76 and 78 are C-shaped and are adhesively attached to their respective C-shaped portions. Contained within sponge members 76 and 78 is an antiseptic solution such as povidone iodine (Betadine). When clasp member 36 is enclosed about connecting device 10, the antiseptic solution disposed within sponges 76 and 78 serves as a sterile barrier to the invasion of microbes.

While the clasp member 36 is designed specifically for use with tubular ports and piercing pins having circular flanges such as 18 and 20, clasp 36 may be used for any conventional I.V. bag connection to provide an aseptic covering of the connection therebetween. Clasp member 36 preferably comprises a modular unit constructed of an injection molded plastic such as polypropylene or other commonly known medical plastics, having an integrally formed hinge 80 between first portion 38 and second portion 40. Latching mechanism 44 preferably comprises male latch members 82 and 84 extending from C-shaped portion 40 and tab 86 and 88 extending from C-shaped portion 38. When first C-shaped portion 38 is pivotally rotated relative to second C-shaped portion 40 by means of the application of digital force, male latches 82 and 84 engage tabs 86 and 83 lock in a closed position until release is desired. However, other commonly known hinges and latch mechanisms may be employed, as well as any suitable medical grade plastic material.

OPERATION OF THE SYSTEM

The invention also includes a method of aseptically sealing the connection between a piercing pin and a tubular port of a medical container. The method comprises the steps of enclosing piercing pin 19 in clasp member 36. Clasp member 36 is then telescopically joined with tubular port 14. During joinder, piercing pin 19, by means of sharpened tip 28, pierces diaphragm 30 within tubular port 14. The assembled tubular port and piercing pin are thereby enclosed in clasp mechanism 36, with sponge members 76 and 78 contained therein which are saturated with an antiseptic solution to prevent microbial contamination. Ratchets 50 prevent inadvertent disconnection.

As best seen in FIG. 2, ratchets 50 are sawtoothed in cross section. Each ratchet 50 has a normal plane 50a extending perpendicularly and inwardly from clasp member 36, and an angular plane 59b extending generally toward the distal end 30 of clasp member 36. When clasp member 36, with piercing pin 19 contained therein is telescoped onto tubular port 14, angular plane 50b slides over flanges 18 and 23. However, once past, normal plane 50a prevents clasp member 36 and thereby piercing pin 19 from being retracted.

The foregoing description and drawings merely explain and illustrate the invention, and the invention is not limited thereto, except insofar as the appended claims are limited to those skilled in the art who have the disclosure before them and are able to make modifications and variations therein without departing from the scope of the invention.

I claim:

1. A connection assembly comprising:
   a medical liquid container;
   a tubular port member extending from the container, said tubular port member including a flange member disposed about its distal end;
   a pierceable diaphragm positioned within and sealing said tubular port member;
   a hollow tubular piercing pin connected at its proximal end to a length of flexible tubing and having a sharpened tip at its distal end adapted for penetration of said pierceable diaphragm member;
   locking means for the selective retention of said piercing pin within said tubular port member;
   said locking means comprising a clasp member including first and second substantially C-shaped body portions hingedly connected to each other and further including latching means at opposing sides thereof, said clasp member being constructed and arranged for telescopic attachment to said tubular port;
   a plurality of protruding frictional engagement means integrally formed and disposed within said clasp member proximate the distal end thereof, said protruding frictional engagement means being constructed and arranged for securing said clasp member on said port following said telescopic attachment; and
   additional engagement means defined by a flange member extending from said piercing pin and a wall surface positioned within said clasp member to limit longitudinal movement of said piercing pin in their direction.

2. The connection assembly as disclosed in claim 1 wherein said clasp member includes a plurality of absorbent sponge members containing an antiseptic solution disposed within each of said substantially C-shaped portions constructed and arranged for asepticizing the connection between said tubular port and said piercing pin.

3. The connection assembly as disclosed in claim 1 wherein said clasp member is constructed and arranged for reception of and engagement with one or more of said flange members so as to fixedly position said connecting device with respect to the telescopic attachment between said piercing pin and said tubular port member.

4. The connection assembly as disclosed in claim 3 wherein said antiseptic solution comprises povidone iodine.

5. The connection assembly as disclosed in claim 1 wherein said protruding frictional engagement means are formed in a sawtooth configuration in cross section, each of said protruding frictional engagement means having a normal plane extending inwardly from said clasp member and an angular plane extending generally in the direction of the proximal end of said first tubular connector whereby said protruding frictional engagement means may slide over said flange on said tubular port when said clasp member is telescoped thereon, but the normal plane of protruding frictional engagement means inpinges upon and locks against said flange member when said clasp member and said tubular port are moved apart, thereby preventing inadvertent separation of said pieceing pin and said tubular port.

* * * * *

UNITED STATES PATENT AND TRADEMARK OFFICE
CERTIFICATE OF CORRECTION

PATENT NO. : 4,432,759

DATED : February 21, 1984

INVENTOR(S) : James R. Gross, et al.

It is certified that error appears in the above—identified patent and that said Letters Patent is hereby corrected as shown below:

Column 6, Claim 1, the last line should read:

in either direction.

Signed and Sealed this

Fifth Day of June 1984

[SEAL]

Attest:

Attesting Officer

GERALD J. MOSSINGHOFF

Commissioner of Patents and Trademarks